United States Patent
Geddes

(10) Patent No.: US 9,829,436 B2
(45) Date of Patent: Nov. 28, 2017

(54) METAL-ENHANCED PHOTOLUMINESCENCE FROM CARBON NANODOTS

(75) Inventor: Chris D. Geddes, Bel-Air, MD (US)

(73) Assignee: Chris Geddes, Bel-Air, MD (US)

( * ) Notice: Subject to any disclaimer, the term of this patent is extended or adjusted under 35 U.S.C. 154(b) by 247 days.

(21) Appl. No.: 14/004,961

(22) PCT Filed: Mar. 19, 2012

(86) PCT No.: PCT/US2012/029609
§ 371 (c)(1),
(2), (4) Date: Feb. 24, 2014

(87) PCT Pub. No.: WO2012/129150
PCT Pub. Date: Sep. 27, 2012

(65) Prior Publication Data
US 2014/0224641 A1  Aug. 14, 2014

Related U.S. Application Data

(60) Provisional application No. 61/454,095, filed on Mar. 18, 2011.

(51) Int. Cl.
| | | |
|---|---|---|
| G01N 21/00 | (2006.01) | |
| G01N 21/64 | (2006.01) | |
| G01N 33/543 | (2006.01) | |
| B01J 19/08 | (2006.01) | |

(Continued)

(52) U.S. Cl.
CPC .......... *G01N 21/6428* (2013.01); *B01J 19/08* (2013.01); *G01N 21/648* (2013.01); *G01N 33/54346* (2013.01); *B82Y 20/00* (2013.01); *B82Y 99/00* (2013.01); *Y10S 977/773* (2013.01); *Y10S 977/953* (2013.01)

(58) Field of Classification Search
None
See application file for complete search history.

(56) References Cited

U.S. PATENT DOCUMENTS

| | | |
|---|---|---|
| 7,095,502 B2 | 8/2006 | Lakowicz et al. |
| 7,400,397 B2 | 7/2008 | Lakowicz et al. |
| 7,718,804 B2 | 5/2010 | Geddes et al. |

(Continued)

FOREIGN PATENT DOCUMENTS

WO   WO2010096414   8/2010

OTHER PUBLICATIONS

Sun, Y.P., et al. Quantum-Sized Carbon Dots for Bright and Colorful Photoluminescence, 2006, Journal of American Chemical Society, vol. 128, pp. 7756-7757.*

(Continued)

*Primary Examiner* — Robert Xu
(74) *Attorney, Agent, or Firm* — Tristan A. Fuierer; Marianne Fuierer; Moore & Van Allen, PLLC

(57) ABSTRACT

The present invention relates to enhancement of detectable emissions from carbon nanodots or variants thereof by using the techniques of MEF to further enhance carbon nanodot brightness, photostability, and thus, potentially detectability in biological imaging applications by using plasmon supporting materials, such as silver island films and positioning of the carbon nanodots an optimal distance from the plasmon supporting materials.

14 Claims, 12 Drawing Sheets

(51) Int. Cl.
  *B82Y 20/00* (2011.01)
  *B82Y 99/00* (2011.01)

(56) References Cited

U.S. PATENT DOCUMENTS

| | | | |
|---|---|---|---|
| 7,732,215 | B2 | 6/2010 | Geddes et al. |
| 7,776,528 | B2 | 8/2010 | Lakowicz |
| 7,939,333 | B2 | 5/2011 | Geddes et al. |
| 7,989,220 | B2 | 8/2011 | Lakowicz et al. |
| 8,008,067 | B2 | 8/2011 | Geddes et al. |
| 8,027,039 | B2 | 9/2011 | Lakowicz et al. |
| 8,034,633 | B2 | 10/2011 | Geddes |
| 8,075,956 | B2 | 12/2011 | Geddes et al. |
| 8,101,424 | B2 | 1/2012 | Geddes |
| 8,114,598 | B2 | 2/2012 | Geddes et al. |
| 8,182,878 | B2 | 5/2012 | Geddes et al. |
| 8,318,087 | B2 | 11/2012 | Geddes |
| 8,338,602 | B2 | 12/2012 | Geddes et al. |
| 8,404,450 | B2 | 3/2013 | Geddes et al. |
| 8,569,502 | B2 | 10/2013 | Geddes et al. |
| 8,618,505 | B2 | 12/2013 | Geddes |
| 8,679,402 | B2 | 3/2014 | Geddes |
| 8,679,855 | B2 | 3/2014 | Geddes |
| 8,722,428 | B2 | 5/2014 | Geddes |
| 8,735,175 | B2 | 5/2014 | Geddes |
| 8,759,110 | B2 | 6/2014 | Geddes |
| 2003/0228682 | A1 | 12/2003 | Lakowicz |
| 2006/0256331 | A1 | 11/2006 | Geddes |
| 2007/0269826 | A1 | 11/2007 | Geddes |
| 2008/0215122 | A1 | 9/2008 | Geddes |
| 2009/0022766 | A1 | 1/2009 | Geddes |
| 2009/0130773 | A1 | 5/2009 | Ayi et al. |
| 2009/0142847 | A1* | 6/2009 | Geddes et al. ............ 436/63 |
| 2009/0325199 | A1 | 12/2009 | Geddes |
| 2010/0003695 | A1 | 1/2010 | Geddes et al. |
| 2011/0020946 | A1 | 1/2011 | Geddes |
| 2011/0207236 | A1 | 8/2011 | Geddes |
| 2012/0021443 | A1 | 1/2012 | Geddes |
| 2012/0028270 | A1 | 2/2012 | Geddes |
| 2012/0107952 | A1 | 5/2012 | Geddes |
| 2012/0282630 | A1 | 11/2012 | Geddes |
| 2013/0115710 | A1 | 5/2013 | Geddes |
| 2013/0156938 | A1 | 6/2013 | Geddes |
| 2014/0030700 | A1 | 1/2014 | Geddes |

OTHER PUBLICATIONS

Sun, Y.P. et al. Doped Carbon Nanoparticles as a New Platform for Highly Photoluminescent Dots, 2008, The Journal of Physical Chemistry C, vol. 112, pp. 18295-18298.*

Tian, L., et al. Nanosized Carbon Particles From Natural Gas Soot, 2009, Chemistry of Materials, vol. 21(13), pp. 2803-2809.*

Aslan, K. et al. Annealed Silver-Island Films for Applications in Metal-Enhanced Fluorescence: Interpretation in Terms of Radiating Plasmons. *J. Fluoresc.*, 2005, 15, 643-654.

Baker, S.N. et al. Luminescent carbon nanodots: emergent nanolights. *Angew. Chem. Int. Ed.* Sep. 2010, 49, 6726-6744.

Dragon, A.I. et al. Excitation volumetric effects (EVE) in metal-enhanced fluorescence. *Phys. Chem. Chem. Phys.*, 2010, 13, 3831-3838.

Geddes, C.D. et al. Metal-Enhanced Fluorescence. *J. Fluoresc.*, 2002, 12, 121-129.

Gonçalves, H. et al. Fluorescent Carbon Dots Capped with $PEG_{200}$ and Mercaptosuccinic Acid. *J. Fluoresc.*, 2010, 20, 1023-1028.

Li, Q. et al. Photoluminescent Carbon Dots as Biocompatible Nanoprobes for Targeting Cancer Cells in Vitro, *J. Phys. Chem. C*, 2010, 114, 12062-12068.

Nune, S.K. et al. Nanoparticles for biomedical imagine, *Expert Opin. Drug Delivery*, 2009, 6, 1175-1194.

Pribik, R. et al. Metal-Enhanced Fluorescence (MEF): Physical characterization of Silver-island films and exploring sample geometries, *Chem. Phys. Lett.*, 2009, 478, 70-74.

Rocco, M. A. et al. Site-specific labeling of surface proteins on living cells using genetically encoded peptides that bind fluorescent nanoparticle probes. *Bioconjugate Chem*, 2009, 20, 1482-1489.

Sun, Y. et al. Quantum-Sized Carbon Dots for Bright and Colorful Photoluminescence, *J. Am. Chem. Soc.*, 2006, 128, 7756-7757.

Xu, X. et al. Electrophoretic Analysis and Purification of Fluorescent Single-Walled Carbon Nanotube Fragments, *J. Am. Chem. Soc.*, 2004, 126, 12736-12737.

Zhang, Y. et al. Wavelength Dependence of Metal-Enhanced Fluorescences. *J. Phys. Chem. C*, 2009, 113, 12095-12100.

Zhang, Y. et al. Metal-Enhanced photoluminescence from carbon nanodots. *Chem. Commun*, 2011, 47, 5313-5315.

* cited by examiner

METAL-ENHANCED PHOTOLUMINESCENCE FROM CARBON NANODOTS

CROSS-REFERENCE TO RELATED APPLICATIONS

This application is filed under the provisions of 35 U.S.C. §371 and claims the priority of International Patent Application No. PCT/US2012/029609 filed on Mar. 19, 2012, which in turn claims priority to U.S. Provisional Patent Application No. 61/454,095, filed on Mar. 18, 2011, the contents of which are hereby incorporated by reference herein for all purposes.

BACKGROUND OF THE INVENTION

Field of Invention

The present invention relates generally to carbon nanodots, and more specifically, to the use of carbon nanodots or variants thereof for replacement of expensive fluorophores or other luminescence labels, wherein signal emissions from excited carbon nanodots is enhanced by close proximity to metallic nanoparticles.

Description of Related Art

The technology of biology has grown from a purely descriptive and phenomenological discipline to that of a set of advanced molecular sciences. Amongst these advances is the use of bio-sensing in technical areas as clinical diagnosis, medicine, and bioengineering. Sensing single or minuet amount of biomolecules and/or chemicals requires integration of the highly selective recognition properties of biomaterials with unique electronic, photonic, and catalytic features of nanomaterials. Proteins, nucleic acid fragments and their biomolecular complexes have nanometric dimensions comparable with the inorganic nanomaterials, of which the inherently high surface-to-volume ratio offers the opportunity for efficient bio-binding and superb sensitivity in detecting biomolecules. A wide range of nanomaterials and sensing techniques, including absorbance (via surface plasmon), electrochemical or electrical, colorimetry, photoluminescence, and chemiluminescence have been explored.

In the last several years, there has been a growing literature on the synthesis and utility of carbon nanodots, also known as carbon nanoparticles.[1-3] Similar to the well-known and commercialized semiconductor quantum dots, the carbon nanoparticles display high quantum yields and photostability, but conversely have low cytoxicity and excellent biocompatibility. Subsequently, these new luminescent labels have found use in biological imaging applications.[4] As with all the new luminescent particle embodiments reported to date, absolute brightness, photostability as well as optical tunability remain primary concerns.

Thus, it would be advantageous to able to use carbon nanodots as a luminescent particle while increasing enhancement of the signal intensity and improving photostability.

SUMMARY OF THE INVENTION

Over the last 10 years, metal-enhanced fluorescence (MEF) has emerged as a technology which directly complements fluorescent labels. In the near-field, within the wavelength of light, luminescent species can interact with metallic surface plasmons in ways which ultimately enhance particle/fluorophore brightness and reduce the excited "system" decay times, which invariably leads to enhanced photostability.

The present invention relates to enhancement of carbon nanodots or variants thereof by using the techniques of MEF to further enhance carbon nanodot brightness, photostability. Thus, carbon nanodots can be used in biological imaging applications by using plasmon supporting materials, such as silver island films[5] and positioning of the carbon dots an optimal distance from the plasmon supporting materials.

In one aspect, the present invention relates to a method for increasing detectable emissions from excited carbon nanodots, the method comprising:

a. providing metallic particles, wherein the metallic particles are immobilized on a surface substrate and the metallic particles include nanostructures, islands or colloids;

b. introducing at least one carbon nanodot or variant thereof for disposing near the metallic particles, wherein the carbon nanodot or variant thereof is capable of emitting a detectable signal upon excitation and positioned from about 5 nm to 200 nm from the metallic particles;

c. applying electromagnetic energy in an amount sufficient to excite the carbon nanodots; and d. measuring the emission from the carbon nanodot or variant thereof, wherein the positioning to the metallic particles increases emissions.

The carbon nanodots (referred also as carbon dots) of the present invention are about 5 nm to about 50 nm in diameter and more preferably from about 5 nm to about 30 nm.

Notably, carbon nanodot variants may include numerous variations, for examples the carbon nanodots may include metallic inclusion, such as doping with metallic materials including silver, gold, copper, aluminum, iron, zinc, rhodium, indium, platinum and combination thereof; doping with dielectric material including metallic oxides; attachments to the carbon surface, such as fluorophores or other luminescent molecules, biomolecules such as nucleotide sequences and proteins; sensitizer molecules attached directly to the carbon dot or a metallic inclusion; dielectric coatings encapsulating the carbon dot having attachment thereto such as other luminescent molecules, biomolecules and/or sensitizers or metallic coating deposited on the dielectric material; metallic coatings deposited directly on the carbon dot surface wherein the metallic coatings having plasmon absorption bands and wherein the metallic coating may further comprise attachment such as antibodies, nucleotide sequences, amino acid residues, or in the alternative a dielectric coating positioned over the metallic coating. Notably if the carbon dot is encapsulated, the encapsulating material can be evenly distributed over the surface or distributed in a non-symmetrical manner. Plasmonic metallic particles can be embedded with the dielectric layer and luminescent molecules attached to the surface of the dielectric material or in the alternative attached to the plasmonic metallic inclusions. Finally, it is envisioned that the carbon nanodots can be embedded or impregnated into a polymeric substrate and such impregnation may also include additional luminescent molecules, while the surface can support biomolecules such as DNA, RNA, proteins, antibodies, etc.

Dielectric materials, such as oxides, may include at least one metal selected from the group consisting of Al, Ca, Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $Al_2O_3$, $SiO_2$, $TiO_2$, $Fe_2O_3$, $CuO$, $ZnO$, $Y_2O_3$, $ZrO_2$, $Nb_2O_5$, $MoO_3$, $In_2O_3$, $SnO_2$, $Sb_2O_5$, $Ta_2O_5$, $WO_3$, $PbO$ or $Bi_2O_3$. These metal oxides may be used alone or in combination with other types of coatings. Preferably, the oxide is a silicon oxide, more preferably, $SiO_2$. The vapor deposition of $SiO_2$ is a well established technique for the controlled deposition of a variety of substrates.

In yet another aspect, the present invention relates to a method of decreasing detection time of a sensing assay used for detection of target molecules, the method comprising:

a. applying a multiplicity of metallic particles to a substrate surface;
b. connecting capture molecules to the metallic particles, wherein the capture molecules have binding affinity for the target molecules;
c. introducing a solution suspected of including the target molecules;
d. introducing detector molecules having affinity for the target molecules, wherein the detector molecules comprises carbon nanodot or a variant thereof and upon binding of detector molecule the carbon nanodot or variant thereof is positioned a distance from about 5 nm to about 50 nm from the metallic particles; and
e. applying electromagnetic energy at a frequency to excite the carbon nanodot or variant thereof; and
f. measuring any emission signal from the excited carbon nanodot or variant thereof.

To further enhance the reaction, the above system may further include applying to the system ultrasound or microwave energy in an amount sufficient to increase movement of the target molecule to the capture molecule thereby causing increased speed of the movement within the system or binding reactions.

Luminescent molecules include compounds or molecules that upon excitation by electromagnetic energy emits detectable emissions, including, but is not limited to fluorophores, chromophores, luminophores, and/or phosphors. A fluorophore compound capable of fluorescing may be an intrinsic fluorophore or a compound attached to an extrinsic fluorophore.

In a still further aspect the present invention relates to a method of metal-enhanced enhancing a detectable signal when sensing of a target molecule, comprising:

a. applying a conductive metallic material to a surface substrate used in a detection system, wherein the surface includes glass, quartz, or a polymeric material;
b. introducing a solution suspected of including the target molecule for disposing near the conductive metallic surface;
c. introducing at least one carbon nanodot or variant thereof that has been functionalize for binding with the target molecules;
d. providing an electromagnetic source to cause excitation and emissions of any of the binding carbon nanodot or variant thereof; and
e. measuring the emission signals from within the system.

The emission enhancement may be observed when the carbon nanodot or variant thereof is positioned from about 5 nm to about 200 nm to metal surfaces. Preferable distances are about 5 nm to about 30 nm, and more preferably, 5 nm to about 20 nm to metal surfaces.

In all embodiments, the metallic material and/or particles may comprise silver, gold, copper, zinc, nickel, iron, rhodium, indium, palladium, aluminum, platinum or any metal exhibiting plasmonic emission. The metallic particles may take the form of metallic islands, colloids, or nanostructures of any geometric shape, such as spherical, triangular, elliptical, rod shape, hexagonal or multifaceted. The metallic material may take the form of porous matrix, metallic particles impregnated within a glass or polymeric surface and/or a metallic surface in a patterned shape.

The patterned shape includes metallic containing shapes having at least one apex wherein the shape includes but is not limited to a triangle, square, rectangle, trapezoid, polygon, elliptical, oblong or combinations thereof. Further, emissions and reactivity can be enhanced by placement of metallic structures having a shape with an apex area and positioning such apex areas adjacent to each other and creating a reactive zone therebetween. The reactive zone therebetween is prepared for placement of the immobilized capture molecule complementary to a target molecule. The metallic structures when fabricated into geometric shapes comprising an apex area for forming a reactive zone can be positioned on assay system with multiple wells wherein the reactive zone includes the wells and exposure to low-intensity ultrasound increases the reactivity and shortens the completion time of the detection assay.

The surface substrate may be fabricated of a polymeric material, glass, paper, nitrocellulose, combinations thereof or any material that provides sufficient stability for placement of the metallic structures.

The present invention relates to a method of detection using plasmonic emissions from metallic surfaces caused by interaction with excited carbon nanodots. These plasmonic emissions emitted from metallic surface plasmons are generated with an external excitation of the carbon dots positioned an optimal distance from the metallic surfaces.

In yet another aspect, the present invention provides a method for detecting a targeted pathogen in a sample, the method comprising:

a. providing a system comprising:
  i. an immobilized metallic material positioned on a surface substrate, wherein the immobilized metallic material has attached thereto an immobilized capture DNA sequence probe complementary to a known DNA sequence of the target pathogen; and
  ii. a free capture DNA sequence probe complementary to a known DNA sequence of the target pathogen, wherein the free capture DNA sequence probe has attached thereto a carbon nanodot or variant thereof;
b. contacting the sample with the immobilized capture DNA sequence probe, wherein the DNA sequence of the target pathogen binds to the immobilized capture DNA sequence probe;
c. contacting the bound DNA sequence of the target pathogen with the free capture DNA sequence probe, wherein binding of the free capture DNA sequence probe to the DNA sequence of the target pathogen causes the carbon nanodot or variant thereof to be positioned a sufficient distance from the immobilized metallic material to enhance emissions due to excitation of the carbon nanodot or variant thereof; and
d. irradiating the system with electromagnetic energy in a range from UV to IR to increase emission by the carbon nanodot or variant thereof positioned a predetermined distance from the metallic material.

To further enhance the reaction, the above system may further include applying to the system ultrasound or microwave energy in an amount sufficient to increase movement of any DNA molecule of the target pathogen to the immobilized probe to enhance binding of the free capture DNA sequence probe to the DNA sequence of the target pathogen thereby causing increased speed of the reactions.

Another aspect of the present invention, relates to a kit for detecting a target molecule in a sample, the kit comprising a. a container comprising a layer of immobilized metal particles deposited on a substrate fabricated of a polymeric or quartz material, wherein an immobilized probe is connected to the metal particles and wherein the immobilized probe has an affinity for the target molecule;
b. a carbon nanodot or variant thereof having an affinity for the target molecule, wherein the binding of the target molecule to both the immobilized probe and carbon nanodot or variant thereof causes the carbon nanodot or variant thereof to be positioned a sufficient distance from the immobilized metal particles to enhance luminescence emission.

In another aspect, the present invention relates to a bioassay for measuring concentration of receptor-ligand binding in a test sample, the method comprising:
a. preparing metallic structures immobilized on a surface wherein the metallic structures have positioned thereon a receptor molecule having affinity for a ligand of interest;
b. contacting the receptor molecule with the test sample suspected of comprising the ligand of interest, wherein the ligand of interest will bind to the receptor molecule to form a receptor-ligand complex;
c. contacting the receptor-ligand complex with a detector molecule having affinity for the ligand to form a receptor-ligand-detector complex, wherein the detector molecule comprises a carbon nanodot or variant thereof;
d. exposing the carbon nanodot or variant thereof to excitation energy in a range from UV to IR to induce an electronically excited state; and
e. measuring the intensity of radiation emitted from exited metallic surface plasmons and/or carbon nanodots or variant thereof.

Preferably, the metallic surfaces take the form of metallic islands, nanostructures, colloids, porous matrix, metallic particles impregnated with a glass or polymeric surface and/or a continuous metallic surface. The metallic element may include any form that exhibits surface plasmons such as noble metals including silver, gold, platinum and copper.

In yet another aspect, the present invention provides for a inducing and measuring current flow comprising:
a. conductive metallic structures positioned on a surface, wherein the metallic structures are shaped as particles, nanostructures, islands or colloids;
b. at least one carbon nanodot or variant thereof for disposing near the conductive metallic structures, wherein the carbon nanodot or variant thereof is capable of inducing a mirror dipole in the metallic structures, wherein the carbon nanodot or variant thereof is positioned from about 5 nm to about 50 nm from the conduction metallic structures;
c. a first and second electrode communicatively connected to at least two of the conductive metallic structures; wherein the first and second electrodes are communicatively connected to a current reading device;
d. an electromagnetic energy source to excite the carbon nanodot or variant thereof and to induce a mirror dipole in the metallic material causing plasmonic current flow, wherein electromagnetic energy source is positioned a distance from the first or second electrode to increase current to be detected by the current reading device,
e. providing a polar solution for covering the conductive metallic structures;

Preferably, the electrodes are separated by a sufficient distance to provide optimal current readings, wherein the separation is from about from about 5 nm to 100 nm. Additionally a polar solvent may be used in the method.

Other aspects and advantages of the invention will be more fully apparent from the ensuing disclosure and appended claims.

DETAILED DESCRIPTION OF THE INVENTION

Figure 1:
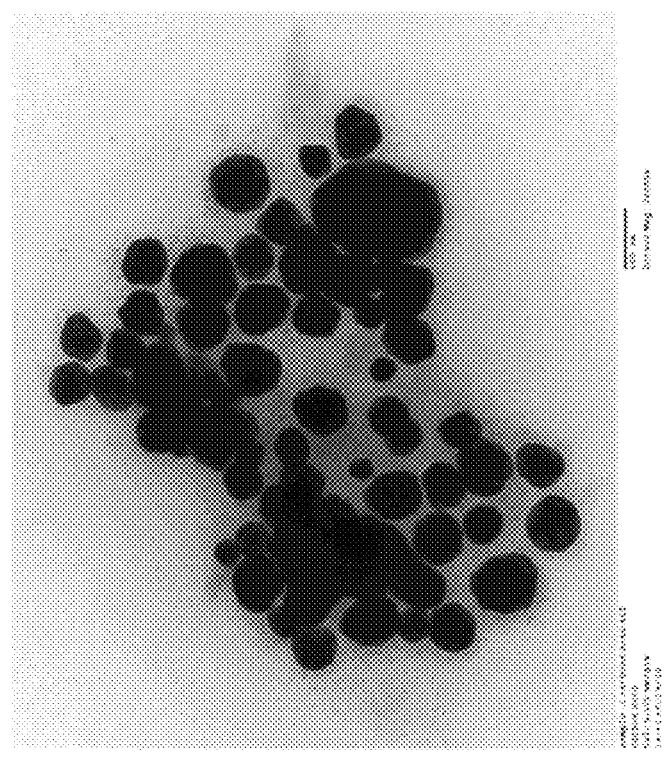
FIG. 1 shows TEM image (right) of carbon dots and absorbance spectrum (left).
Figure 1:
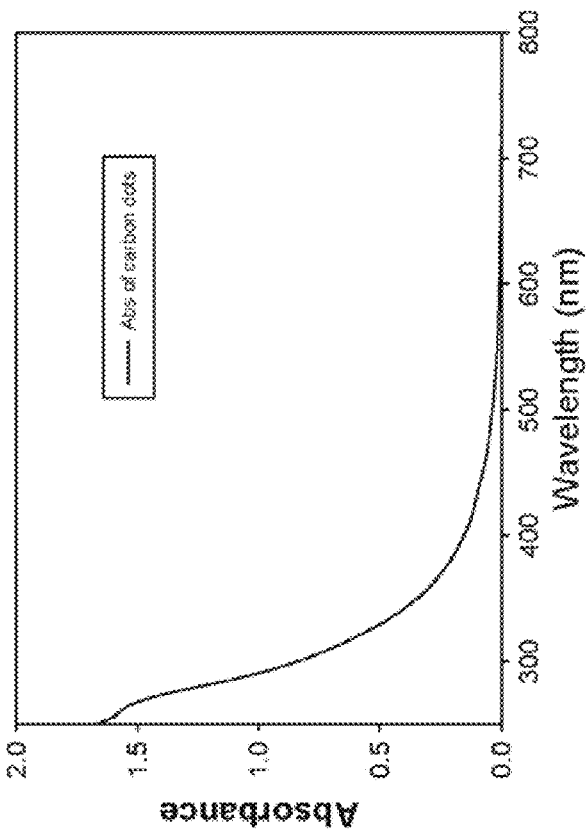

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide nucleic acids, fatty acids, sugar groups such as glucose etc., vitamins, cofactors, purines, pyrimidines, formycin, lipids, phytochrome, phytofluor, peptides, lipids, antibodies and phycobiliproptein.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, infection or specific assay.

Fluorophore," and "fluorescence label," used interchangeably herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™, naphthalamine sulfonic acids including but not limited to 1-anilinonaphthalene-8-sulfonic acid (ANS) and 6-(p-toluidinyl) naphthalen-e-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2[(di-n-butylamino)-6 naphthyl]vinyl]pyridinium betaine (Naphtyl Styryl), 3,3' dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrimidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

Fluorophores with high radiative rates have high quantum yields and short lifetimes. Increasing the quantum yield requires decreasing the non-radiative rates $k_{nr}$, which is often only accomplished when using a low solution temperature or a fluorophore bound in a more rigid environment. The natural lifetime of a fluorophore, $\tau_n$, is the inverse of the radiative decay rate or the lifetime which would be observed if their quantum yields were unity. This value is determined by the oscillator strength (extinction coefficient) of the electronic transition. Hence, for almost all examples currently employed in fluorescence spectroscopy, the radiative decay rate is essentially constant. The modification and control of the radiative rate have also been referred as Radiative Decay Engineering (RDE), or "lightening rod" fluorescence enhancement effect. For example, enhanced intrinsic DNA fluorescence above metallic particles has recently been observed, which is typically not readily observable because of DNA's very low quantum yield of less than $10^{-4}$. The second favorable "lightening rod" effect also increases the fluorescence intensity by locally enhanced excitation. In this case, emission of fluorophores can be substantially enhanced irrespective of their quantum yields.

The reduction in lifetime of a fluorophore near a metal is due to an interaction between the fluorophore and metal particle, which enhances the radiative decay rate (quantum yield increase) or depending on distance, $d^{-3}$, causes quenching. It should be noted that lifetimes of fluorophores with high quantum yields (0.5) would decrease substantially more than the lifetimes of those with low quantum yields (0.1 and 0.01). A shorter excited-state lifetime also allows less photochemical reactions, which subsequently results in an increased fluorophore photostability. Notably, the use of low quantum yield fluorophores would lead to much larger fluorescence enhancements (i.e. $1/Q_0$) and could significantly reduce unwanted background emission from fluorophores distal from the silvered assay.

Photostability is a primary concern in many applications of luminescence. This is particularly true in single molecule spectroscopy. A shorter lifetime also allows for a larger photon flux. The maximum number of photons that are emitted each second by a carbon nanodot is roughly limited by the lifetime of its excited state. For example, a 10 ns lifetime can yield about $10^8$ photons per second per molecule, but in practice, only $10^3$ photons can be readily observed. The small number of observed photons is typically due to both photo-destruction and isotropic emission. If a metal surface decreases the lifetime, one can obtain more photons per second per molecule by appropriately increasing the incident intensity.

On the other hand, the metal-enhanced luminescence provides enhanced intensity, while simultaneously shortening the lifetime. That is, it may be possible to decrease the excitation intensity, yet still see a significant increase in the emission intensity and photostability.

The emission enhancement may be observed when a carbon nanodot is distanced about 5 nm to about 200 nm to metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Attaching of the carbon nanodot or variant thereof to a probe may be achieved by any of the techniques familiar to those skilled in the art.

Techniques for attaching antibodies or antigens to solid substrates are also well known in the art. For example, antibodies may be coupled covalently using glutaraldehyde to a silane derivative of borosilicate glass.

Figure 6:
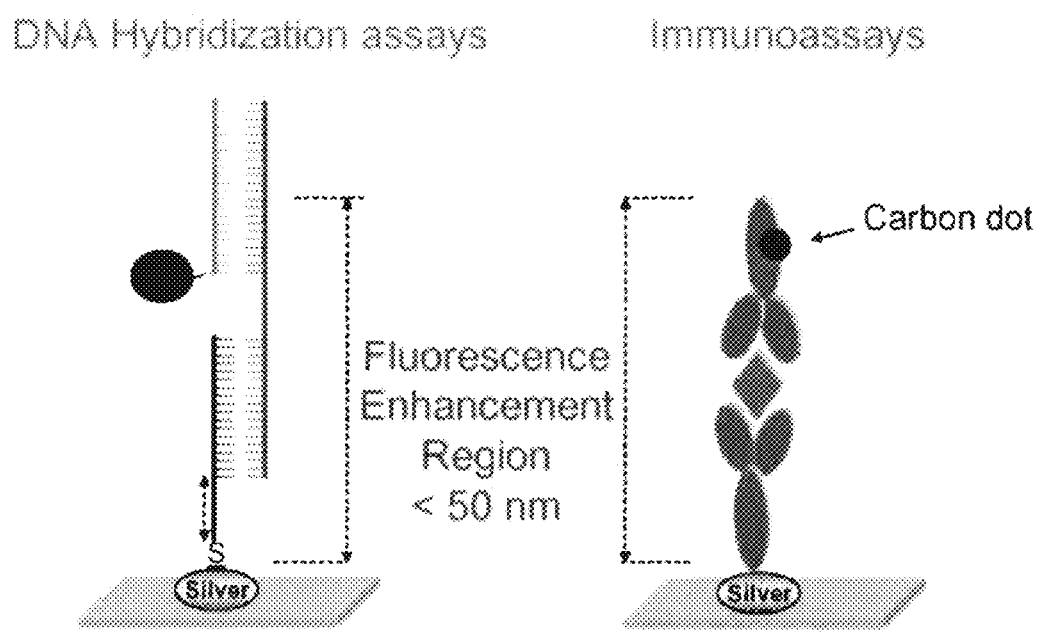
FIG. 6 shows that when either the DNA/RNA or Antibody based assay is complete, the carbon nanodot is located near-to the silver surface, which causes significantly enhanced carbon nanodot luminescence, facilitating the assays sensitivity. This figure shows the case for both a 3-piece DNA hybridization assay as well as an Antibody-antigen assay.

In another embodiment, the present invention relates to detection of a nucleotide sequence from a target molecule. A testing for a nucleotide sequence within a sample can be identified and quantified by attachment of a nucleotide capture probe on a metallic particle. Once the target nucleotide sequence attaches to the capture probe, a detection nucleotide probe including a carbon nanodot of the present invention can be used to identify and wherein emission signals from an excited carbon nanodot are enhanced by the silver nanoparticles as shown in nucleotide sensing platform system of FIG. 6.

"Nucleotide," as used herein refers to deoxyribonucleic acid (DNA) or ribonucleic (RNA), RNA can be unspliced or spliced mRNA, rRNA, tRNA, or antisense RNAi. DNA can be complementary DNA (cDNA), genomic DNA, or an antisense.

The nucleotides used as hybridization probes in the present inventor are typically designed to be specific for the desired sequence in order to decrease the probability of hybridizing to unrelated sequences. Such probes can be modified so as to be detectable using radionuclides, luminescent moieties, and so forth. Hybridization conditions also can be modified in order to achieve the desired specificity. For example, a moderately stringent hybridization condition may include: 2×SSC/0.1% SDS at about 37° C. or 42° C. (hybridization conditions); 0.5×SSC/0.1% SDS at about room temperature (low stringency wash); 0.5×SSC/0.1% SDS at about 42° C. (moderate stringency wash). An example of moderately-high stringency hybridization conditions is as follows: 0.1×SSC/0.1% SDS at about 52° C. (moderately-high stringency wash). An example of high stringency hybridization conditions is as follows: 0.1×SSC/0.1% SDS at about 65° C. (high stringency wash).

The nucleotides sequences of the present invention can be obtained using standard techniques known in the art (e.g., molecular cloning, chemical synthesis) and the purity can be determined by polyacrylamide or agarose gel electrophoresis, sequencing analysis, and the like. Polynucleotides also can be isolated using hybridization or computer-based techniques that are well known in the art. Such techniques include, but are not limited to: (1) hybridization of genomic DNA or cDNA libraries with probes to detect homologous nucleotide sequences; (2) antibody screening of polypeptides expressed by DNA sequences (e.g., using an expression library); (3) polymerase chain reaction (PCR) of genomic DNA or cDNA using primers capable of annealing to a nucleic acid sequence of interest; (4) computer searches of sequence databases for related sequences; and (5) differential screening of a subtracted nucleic acid library.

Increasing a binding reaction of the present invention may be achieved by using any device capable of generating and transmitting acoustic energy through any medium to transit ultrasonic atomizing energy. The ultrasonic emitting device can be placed in either the interior of a vessel or positioned adjacent thereto for transmitting energy into the vaporization vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$: $R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

The assay systems of the present invention may further comprise a light or laser source for directing an energy beam on any included excitable molecule to provide excitation energy. The laser beam may be positioned adjacent to the system for directing the beam at the molecular components. The laser may be any device capable of focusing an energy beam at a particular point on the solid or liquid source material for excitation and the laser may transmit RF, infrared, microwave to UV energy.

Further, excitation light sources can include arc lamps and lasers, laser diodes and light emitting diode source, and both single and multiple photon excitation sources. In another embodiment, use of a Ti-sapphire laser, Laser Diode (LD) or Light Emitting Diode Sources (LEDs) may be used with the RNA assay of the present invention. For example, using 2-photon excitation at 700-1000 nm and also using short pulse width (<50 pi), high repetition rate (1-80 MHz), laser diode and LED (1 ns, 1-10 MHz) sources. The enhanced sensitivity of the assay using 2-photon excitation, as compared to 1-photon, can be shown by using series dilution with RNA, initially with the Ti-Sapphire system, and later with LEDs and LDs. If a carbon nanodot absorbs two photons simultaneously, it will absorb enough energy to be raised to an excited state. The carbon nanodot will then emit a single photon with a wavelength that depends on the carbon dot or variant thereof used and typically in the visible spectra. The use of the Ti-sapphire laser with infrared light has an added benefit, that being, longer wavelengths are scattered less, which is a benefit to high-resolution imaging. Importantly, there is reduced background signal level gained by using 2-photon excitation as compared to 1-photon excitation by utilizing localized excitation nearby metallic particles.

Any source, known to one skilled in the art may be used, such as a laser that emits light, wherein light is used in its broad sense, meaning electromagnetic radiation which propagates through space and includes not only visible light, but also infrared, ultraviolet radiation, acoustic or microwave energy. Thus, a single instrument placed above the surface of the assay can be used to generate energy to excite carbon nanodots in addition to sonic or microwave energy. The light or sound waves can be emitted from a fiber continuously or intermittently, as desired, to increase the speed of chemical reactions within the assay system.

In one embodiment, the application of low level microwave heating of the sample may be used to speed up any chemical/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the metallic structures, which is contrary to most metal objects, such as that recognized by placing a spoon in a microwave oven.

Microwaves (about 0.3 to about 300 GHz) lie between the infrared and radiofrequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether. For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles. Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metallic structures in addition to the heating of any surface polar molecules. Intuitively, this leads to localized heating around the metallic structures in addition to the solvent, rapidly accelerating assay kinetics.

In the present invention, microwave radiation may be provided by an electromagnetic source having a frequency in a range between 0.3 and 10 GHz and a power level in a range between about 10 mwatts and 400 watts, more preferably from 30 mwatts to about 200 watts. Any source, known to one skilled in the art may be used, such as a laser that emits light, wherein light is used in its broad sense, meaning electromagnetic radiation which propagates through space and includes not only visible light, but also infrared, ultraviolet and microwave radiation. Thus, a single instrument placed above the surface of the assay can be used to generate the microwave energy and energy to excite the carbon nanodots or variants thereof. The light can be emitted from a fiber continuously or intermittently, as desired, to maintain the metallic particles at a predetermined temperature such that it is capable of increasing the speed of chemical reactions within the assay system. The microwave radiation may be emitted continuously or intermittently (pulsed), as desired. In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

Emitting energy signals can be detected using devices including, but not limited to, a spectrofluorometer having a light source and detector. Detectors can include photomultiplier tubes. Additionally, it is advantageous for the device to have a monochromator so that specific wavelengths of light may be used to excite a molecule or to detect emissions at a specific wavelength.

Preparation of Metal Islands

The island particles are prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available. Silver is primarily used because of the familiar color from the longer surface plasmon absorption of silver.

Preparation of Silver Colloids

Colloids can be prepared as suspensions by citrate reduction metals. Preferred metals are silver and gold. Again, gold may be because of the absorption of gold at shorter wavelengths.

The size of the colloids and their homogeneity can be determined by the extensive publications on the optical properties of metal particles available and the effects of interface chemistry on the optical property of colloids.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

In one embodiment, detection occurs without binding the molecules to the sensor or support. The molecule to be detected is not chemically bound. The molecule to be detected may remain in solution and not directly or indirectly interact with the metal particles, coatings or film spacer layers.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

Polymers containing metal particles may have other applications, including but not limited to, size inclusion/exclusion sensing of non-fluorescent species, increased photostability of embedded carbon nanodots, single pore single molecule detection, and porous polymers which allow diffusing analytes or antibodies, resulting in a detectable and quantifiable signal change in the analyte or antibody or respective transduction element.

The embodiments of the present invention may have vast applications in clinical medicine, environmental monitoring applications, homeland security such as rapid detection of low concentration species, industrial processes, pharmaceutical industries such as monitoring species, and sensors for use in reduced atmospheres such as biohazard clean rooms and space light.

EXAMPLES

Over the last 10 years, metal-enhanced fluorescence (MEF) has emerged as a technology which directly complements fluorescent labels. In the near-field, within the wavelength of light, luminescent species can interact with metallic surface plasmons in ways which ultimately enhance particle/fluorophore brightness and reduce the excited "system" decay times, which invariably leads to enhanced photostability.

For a fluorescent species in the far-field condition, i.e. more than 1 wavelength of light away from either a surface or particle, the quantum yield of a fluorophore is given by:[6]

$$Q_0 = \frac{\Gamma}{\Gamma + K_{nr}} \quad (1)$$

where $\Gamma$ is the fluorophores' radiative decay rate and $K_{nr}$ are the nonradiative decay rates for excited state relaxation. In the presence of metal, i.e. near-field condition, it has been shown that the system quantum yield, $Q_m$, can readily be defined by:[6]

$$Q_m = \frac{\Gamma + \Gamma_m}{\Gamma + \Gamma_m + K_{nr}} \quad (2)$$

where $\Gamma_m$ is the system modified radiative rate. Similarly, both far- and near-field lifetimes are given by:

$$\tau = \frac{1}{\Gamma + K_{nr}} \quad (3)$$

$$\tau_m = \frac{1}{\Gamma + \Gamma_m + K_{nr}} \quad (4)$$

Interestingly, by increasing $\Gamma_m$ in as shown in equation (2) and (4), i.e. the near-field condition, MEF readily affords for increased system quantum yields and reduced decay times, i.e. enhanced photostability. This is in contrast to the far-field condition, where the lifetime and quantum yield change in unison. In these equations, metal-modified non-radiative rates is not accounted for and while some authors have reported very-close proximity quenching, Geddes' have recently hypothesized that these reductions in close range luminescent intensities are in fact due to changes in the near-field electric field distributions, which are substrate specific.

Polyethylene Glycol (PEG) terminated carbon dots were synthesized as previously reported.[1] Excitation of the carbon dots was undertaken using a Spectrofluorometer Fluoromax 4 for excitation dependence studies, and using 405, 473 and 532 nm laser lines for the MEF studies, where an ocean optics HD 2000+ Spectrometer with a 600 μm fiber bundle was used for the collection of fluorescence emission. The preparation of SiFs has been reported previously.[8] Fluorescence lifetimes of the carbon dots from both SiFs surfaces and glass substrates (a control sample containing no silver) were undertaken using the Time-Correlated Single Photon Counting Technique (TCSPC) with a 400 nm laser for excitation and a TBX-4 module for detection. Deconvolution analysis of the respective luminescence decays was performed using DAS 6.0 software. The calculation of the mean τ and amplitude weighted lifetimes <τ> has been reported previously.[8]

Figure 2:
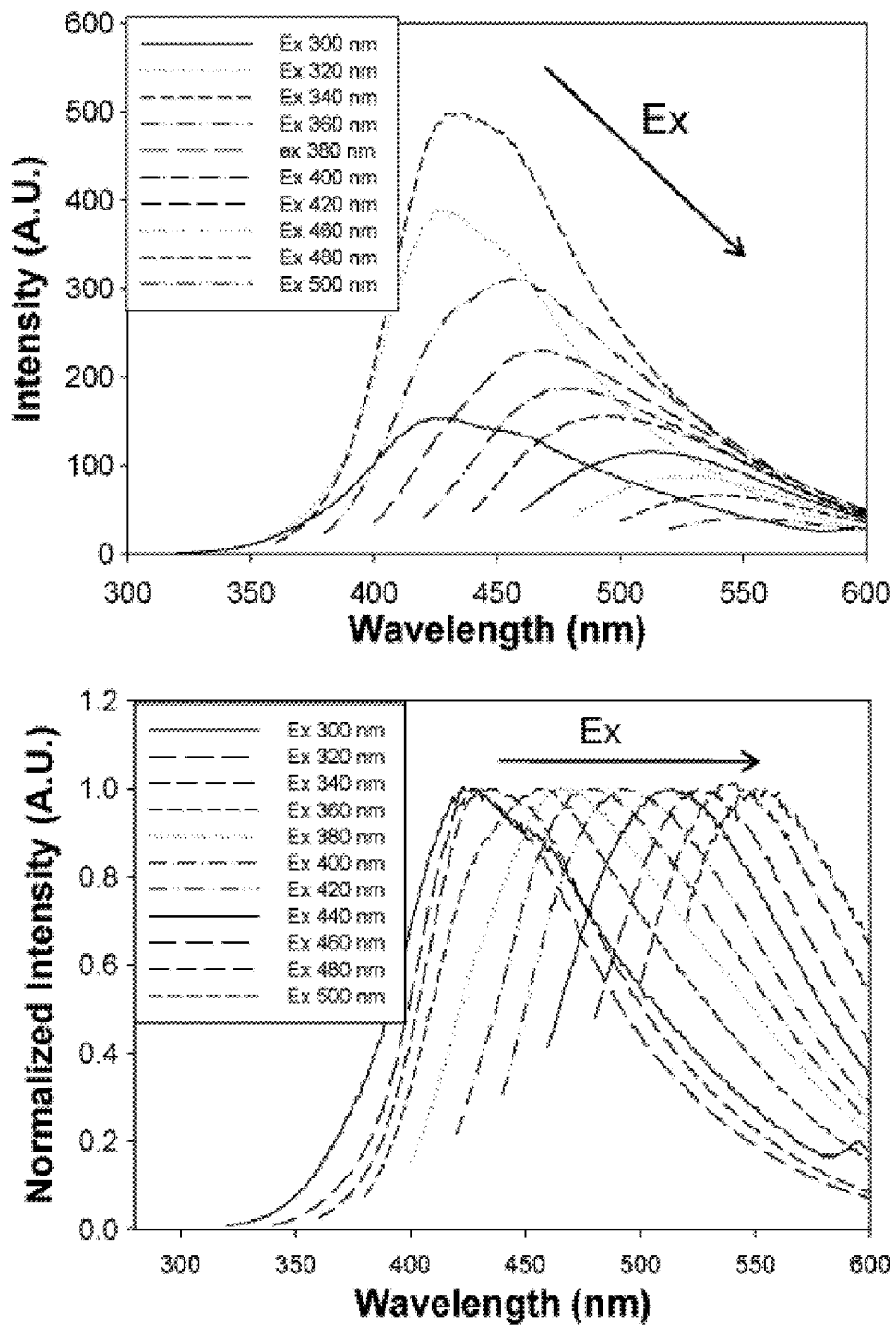
FIG. 2 shows fluorescence emission spectra (top) and normalized emission spectra (bottom) of carbon dots for different excitation wavelength.

FIG. 1 (right) shows a typical TEM image of the carbon dots, where the size of the dots appears to be in the range of 50-80 nm. The optical absorption of the carbon nanodots is primarily in the UV and tails out beyond 500 nm, FIG. 1—left. Interestingly, the dots show an excitation wavelength and quantum yield dependence, FIG. 2, with the luminescence quite weak when excited beyond 500 nm. The spectral width of the emission is also very similar when normalized, FIG. 2 (bottom). The mechanism of photoluminescence from carbon dots was attributed to the presence of surface energy traps that become emissive upon stabilization as a result of the surface passivation. These findings suggest that the spectral properties are dependent on not only the particle size but also a distribute of different emissive sites on each passivated carbon dots.[9]

Figure 3:
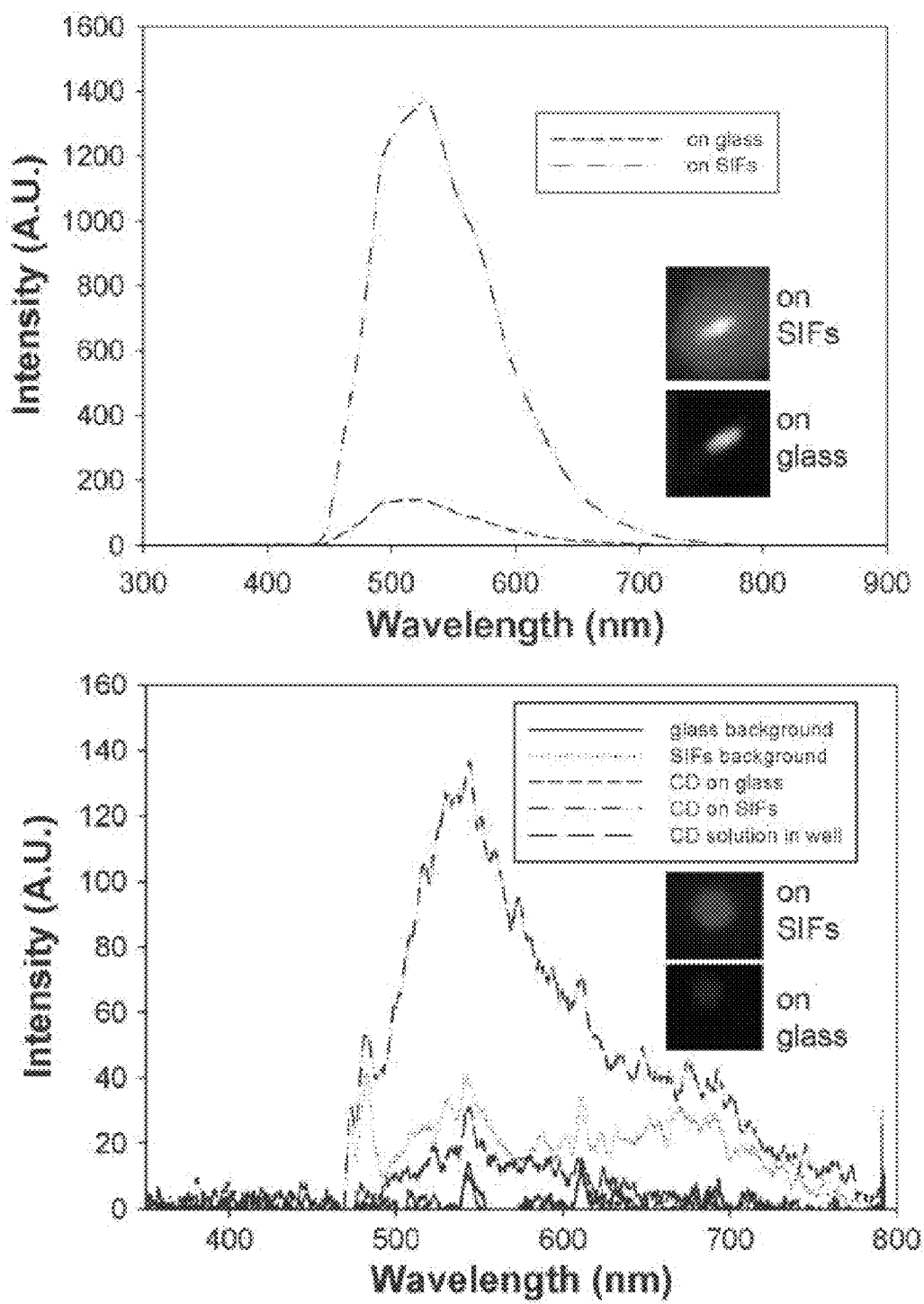
FIG. 3 shows fluorescence emission spectra of carbon dots with 1Ex=405 nm CW laser from both a SiFs surface and also from a glass control sample (top). Fluorescence emission spectra of carbon dots with 1Ex=473 nm (bottom). Real color photographs were taken through a 473 nm razor edge filter.
Figure 4:
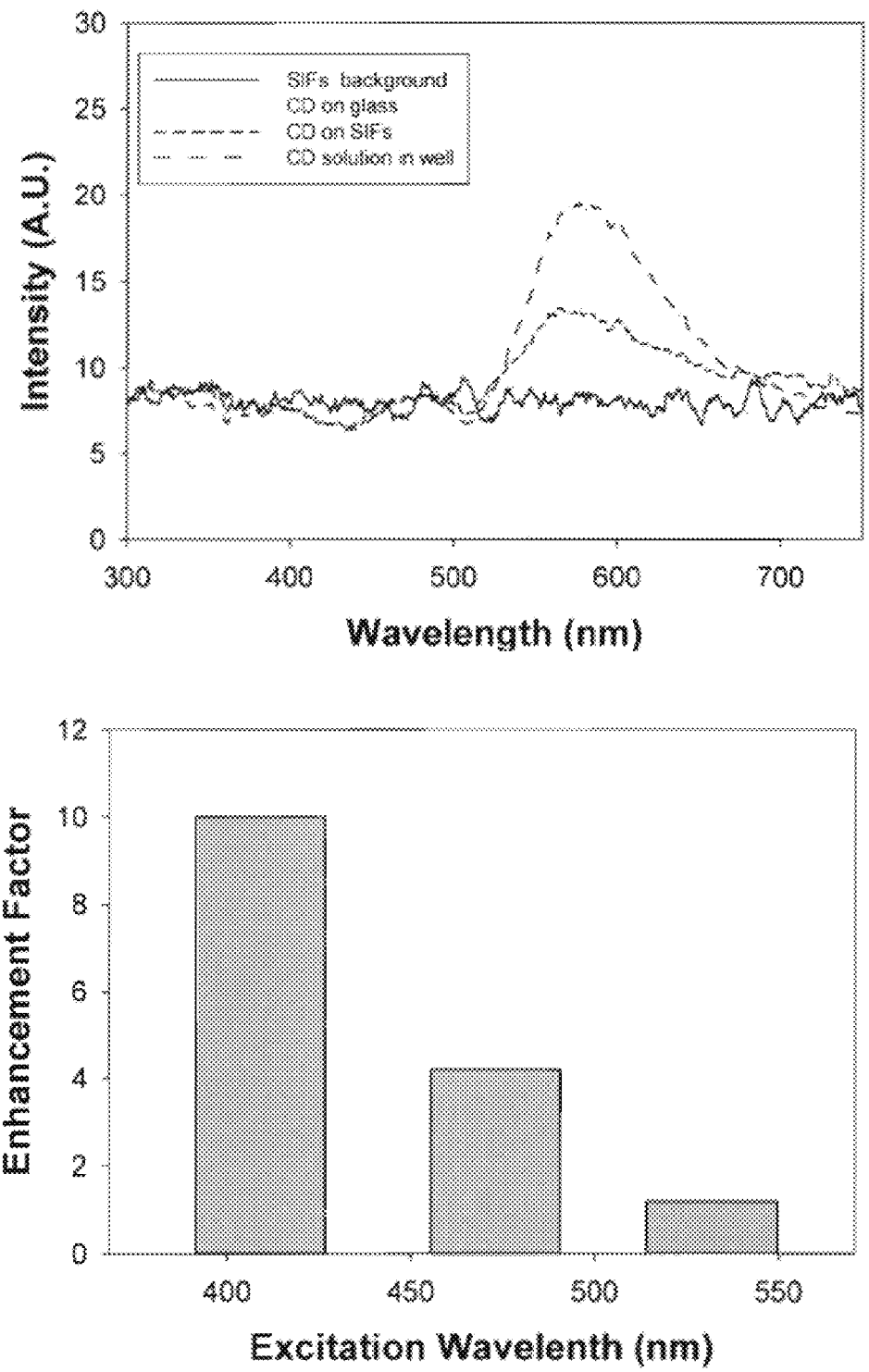
FIG. 4 shows fluorescence emission spectra of carbon dots with 1Ex=532 nm laser from both SiFs and a glass control sample (top). Enhancement factor vs. excitation wavelength: 405 nm, 473 nm and 532 nm (bottom). Enhancement factor was calculated as the ratio between the emission from the SiFs substrate divided by that observed from an otherwise identical control sample (glass), containing no metal.

When solutions of the nanodots were excited on SiFs (silver island films), significantly enhanced luminescence could be seen, FIG. 3—top, and photograph insets. At an excitation wavelength of 405 nm, over a 10-fold increase in luminescence could be observed as compared to an otherwise identical control sample, but which contained no silver. FIG. 3 (bottom) shows the emission from carbon dots on SiFs and control glass substrate (containing no silver nanoparticles) at the excitation wavelength of 473 nm. Over 4-fold increase in luminescence could be observed. Furthermore, the results in FIG. 4 (top) shows a 1.5-fold enhancement factor of carbon dots on SiFs with excitation wavelength 532 nm. Similar to the free space condition, the emission intensity is reduced with increasing wavelength, with very little enhanced luminescence observed when excited at 532 nm, FIG. 4—bottom. The near-field volume changes non-linearly with far-field power, in FIG. 4—bottom.

Figure 5:
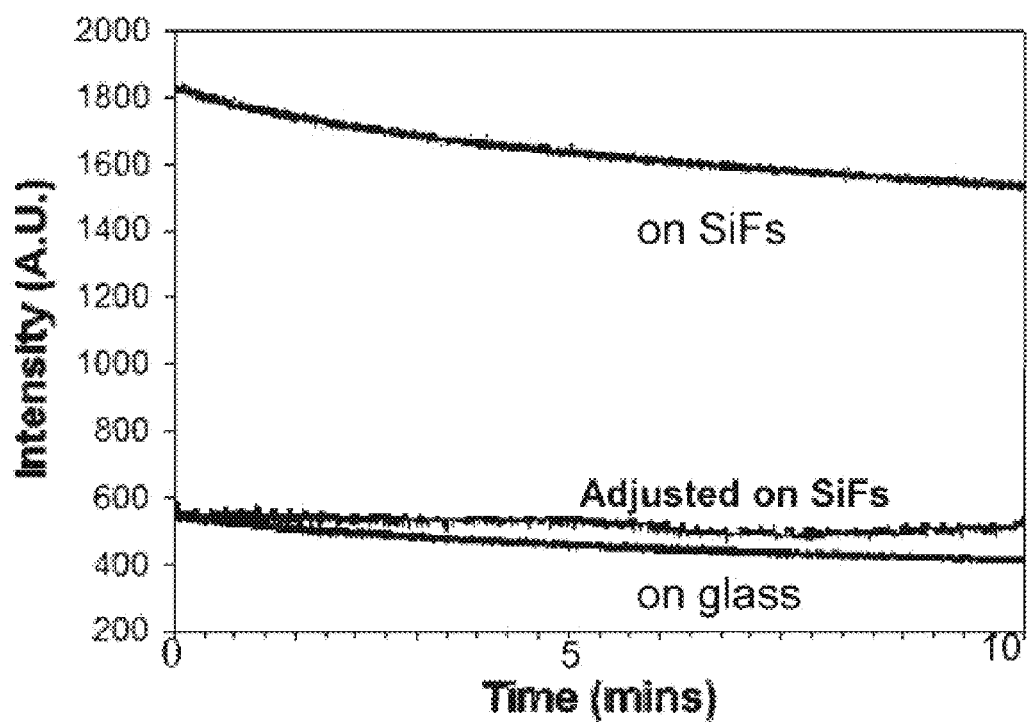
FIG. 5 shows emission intensity vs. time, photostability of carbon dots on SiFs and glass and with the laser power adjusted to give the same initial steady-state fluorescence intensity as observed on glass (bottom traces). SiFs—silver island films.

The time-resolved decay times for carbon dots in both the far and near-field conditions were measured as shown in Table 1, set forth below. The lifetime of the dots is multi-exponential in solution with mean and amplitude weighted lifetimes of 2.09 and 5.65 ns respectively. In the near field, i.e. on SiFs, these values significantly decrease to 1.53 and 0.26 ns, respectively, which is consistent with current MEF thinking and equation (2) and (4). Subsequently, the photostability of carbon dots has been studied from both the control sample and the SiFs surface. On the SiFs surface one readily sees more emission vs. time, i.e. photon flux, which is proportional to the integrated area under the curve, as shown in FIG. 5. From the glass substrate it can be readily see that there is significantly less luminescence, which photobleaches more rapidly than the adjusted SiFs substrate, as shown in FIG. 5. This increase in photostability from SiFs is consistent with the reduced lifetime on SiFs, as shown in Table 1 and equation (4), where luminescent species in an excited state are less prone to excited state photophysics if the decay time is shorter.

dielectric inclusions (D) can be embedded in the carbon material. The surface of the carbon nanodot can be functionalized to support antibodies (C) and (E).

Figure 8:
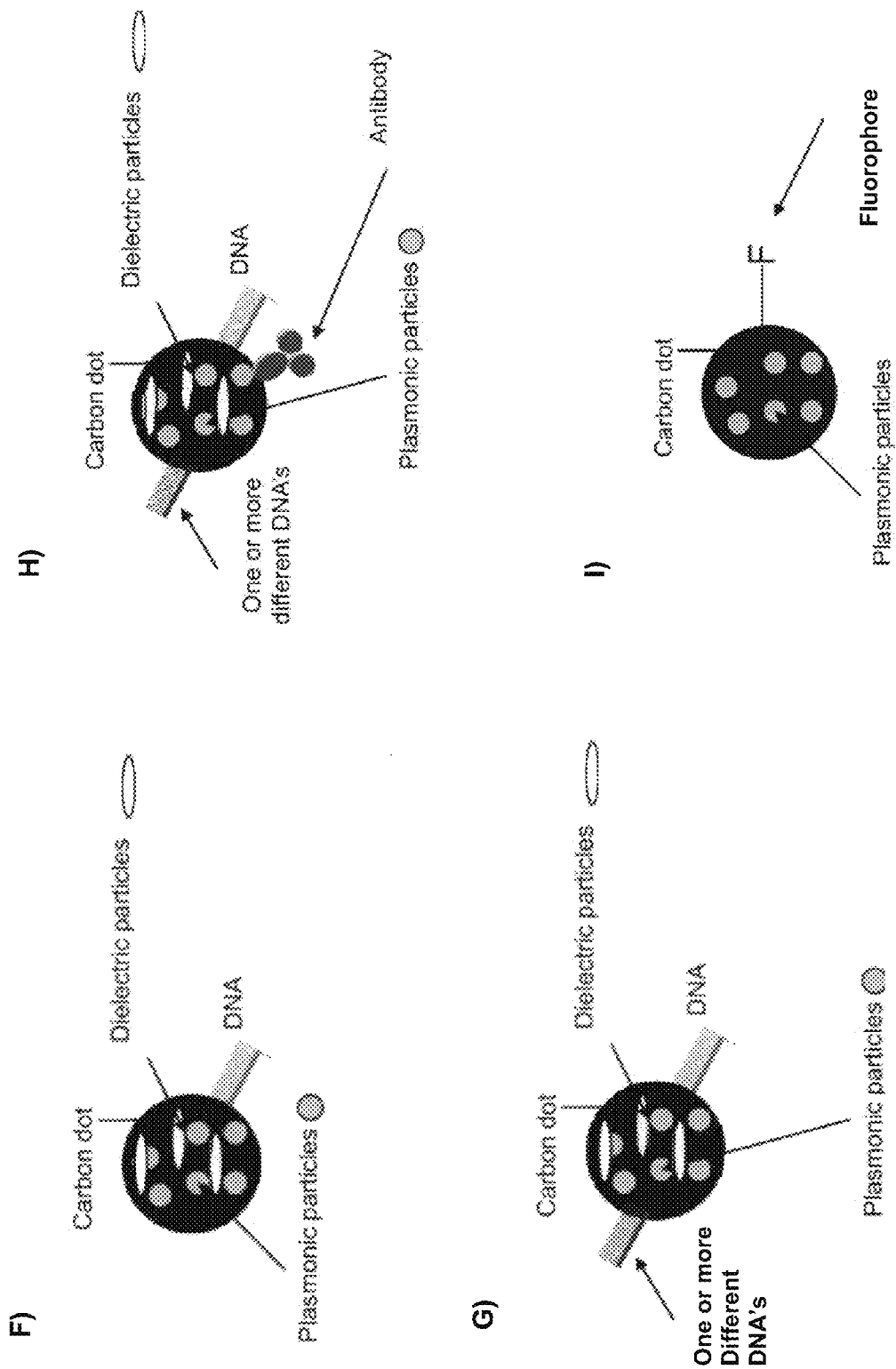
FIG. 8 shows different embodiments of carbon dots showing attachments of nucleotide sequences and/or fluorophores to the surface of the carbon dots.
Figure 9:
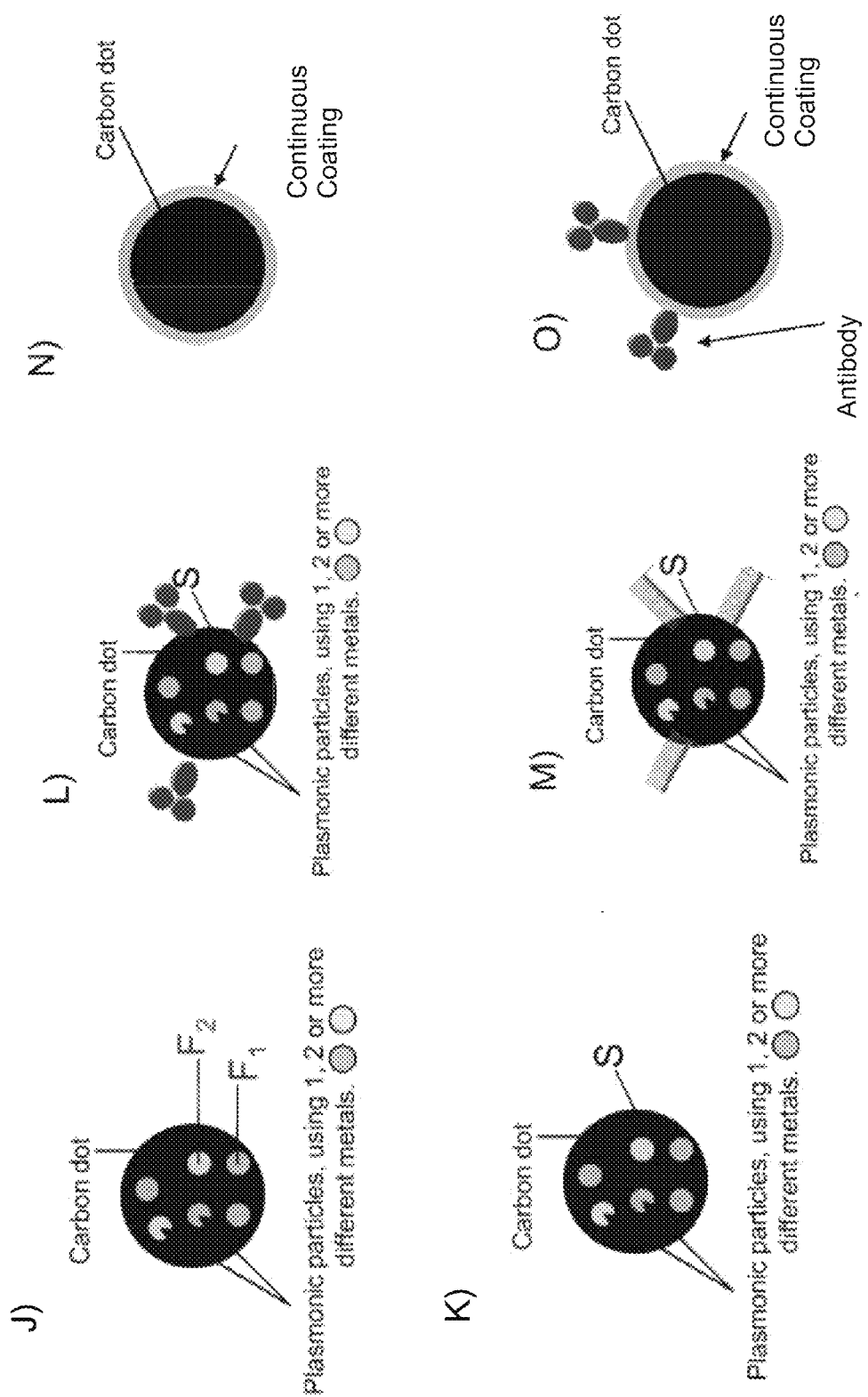
FIG. 9 shows different embodiments of carbon dots showing attachments of antibodies and/or sensitizing compounds attached to the surface. Further, carbon dots are shown having a continuous coating on the surface of the carbon dot.

As shown in FIG. 8, the surface of the carbon nanodot can be functionalize to support nucleotide sequences for identifying target DNA in a solution, such as in an assay (F). The DNA can be anchored to either the metallic plasmonic inclusion or on the carbon surface. As shown in FIG. 8(I) additional light emitting molecules, such as fluorophores may also be attached to the carbon surface. FIG. 9(J) shows that multiple fluorophores may be attached to either the metallic particles or directly on the carbon surface. Further, additional molecules may be attached, such as a sensitizer molecule, attached to the surface of either the metallic inclusion or carbon surface, wherein the sensitizer molecule is triplet pumped by close proximity to the metal for enhanced singlet oxygen and/or superoxide anion radical generation. As shown in FIG. 9 (L) and (M) surface immobilized antibodies, DNA or RNA can be used to direct the carbon nanodots to places of interest such as to tissues, cancer cells, lesion, etc.

Figure 10:
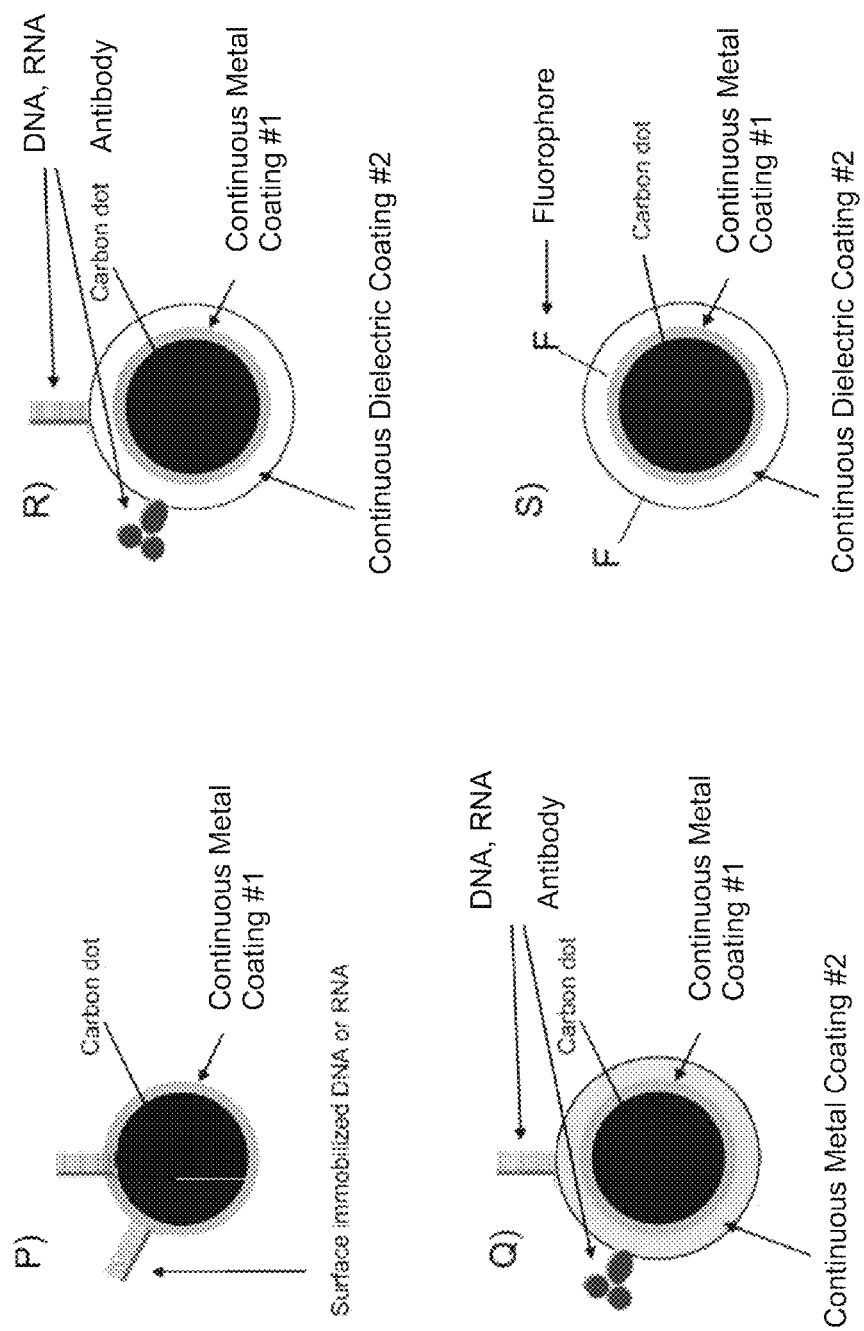
FIG. 10 shows different embodiments of carbon dots wherein multiple layers of coating may be applied to the carbon dots and surface attachments such as DNA, RNA, antibodies and/or fluorophore.

FIG. 9 also shows variations wherein the carbon nanodot can be coated with a continuous metallic film of plasmonic metal (N) and can be further functionalized by adding antibodies (O). FIG. 10 (P) shows that nucleotide sequences can also be immobilized on the metallic coating. As shown in FIG. 10(Q) the first metal coating can be covered with a second metal coating and this second coating can be functionalized with nucleotides or protein type material.

Figure 11:
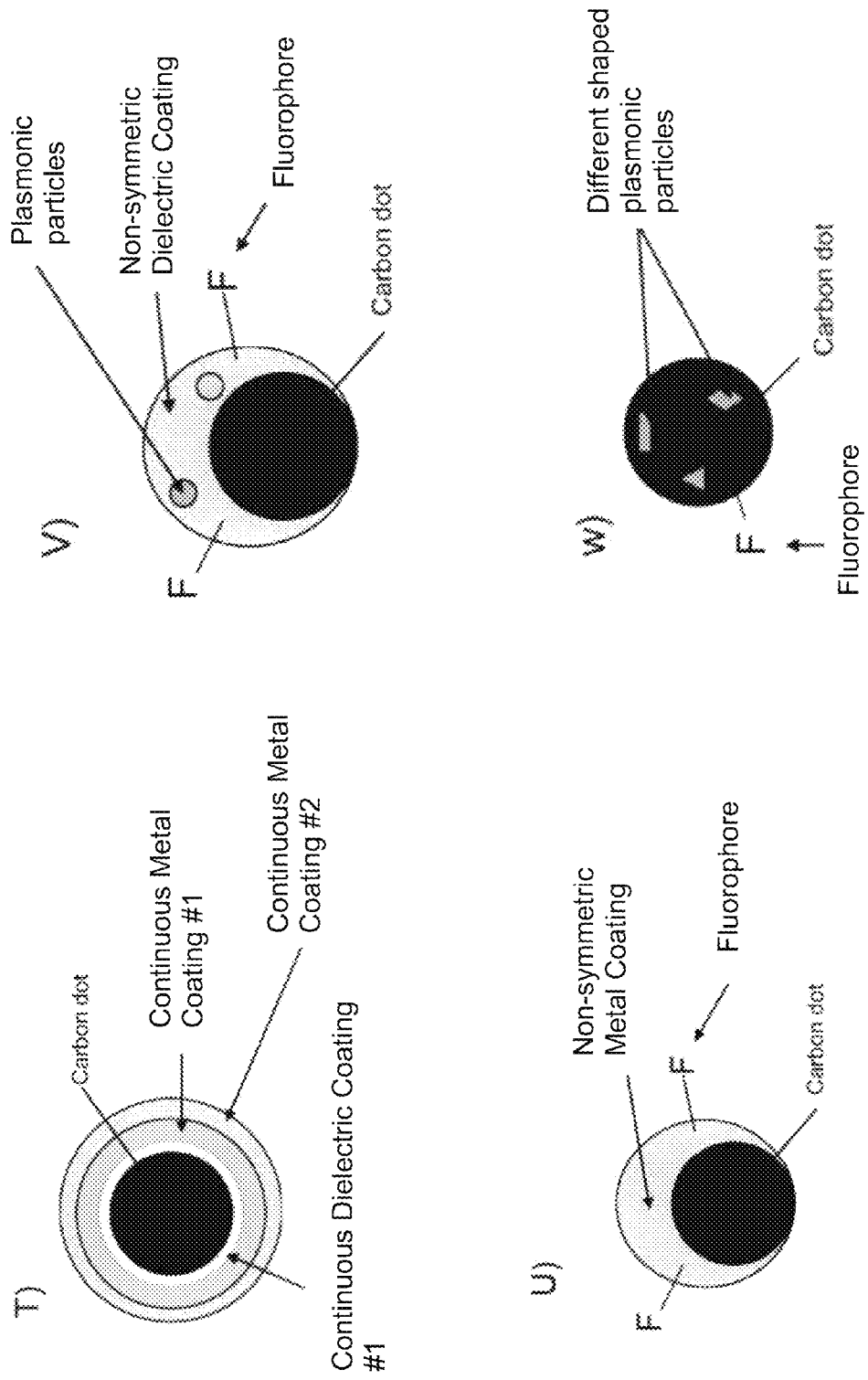
FIG. 11 shows different embodiments of carbon dots wherein a coating may be applied in a non-symmetric layer and with inclusions of plasmonic particles. Further, the carbon dots may include different shaped plasmonic particles position on the surface or embedded in the carbon dots.

FIG. 10 (R) and (S) show that the second metal coating can be replaced with a coating fabricated of a dielectric material, wherein the dielectric materials usable for this purpose have been previously described. Again the coating can be adapted for carrying nucleotide sequences, antibodies and fluorophores. FIG. 11 (T) shows that a dielectric coating can be deposited directly on the carbon nanodot surface and with additional metallic coating thereon.

FIG. 11 (U) shown that a metallic plasmonic coating on the carbon dot can be applied in a non-symmetrical manner. Further the non-symmetrical coating can be fabricated of a dielectric material and such dielectric material may be impregnated with metallic plasmonic inclusions (V). FIG. 11 (W) shows that the plasmonic metallic particles may be attached directly to the surface and can be different shapes, such as triangle, rectangle, or trapezoid.

Figure 12:
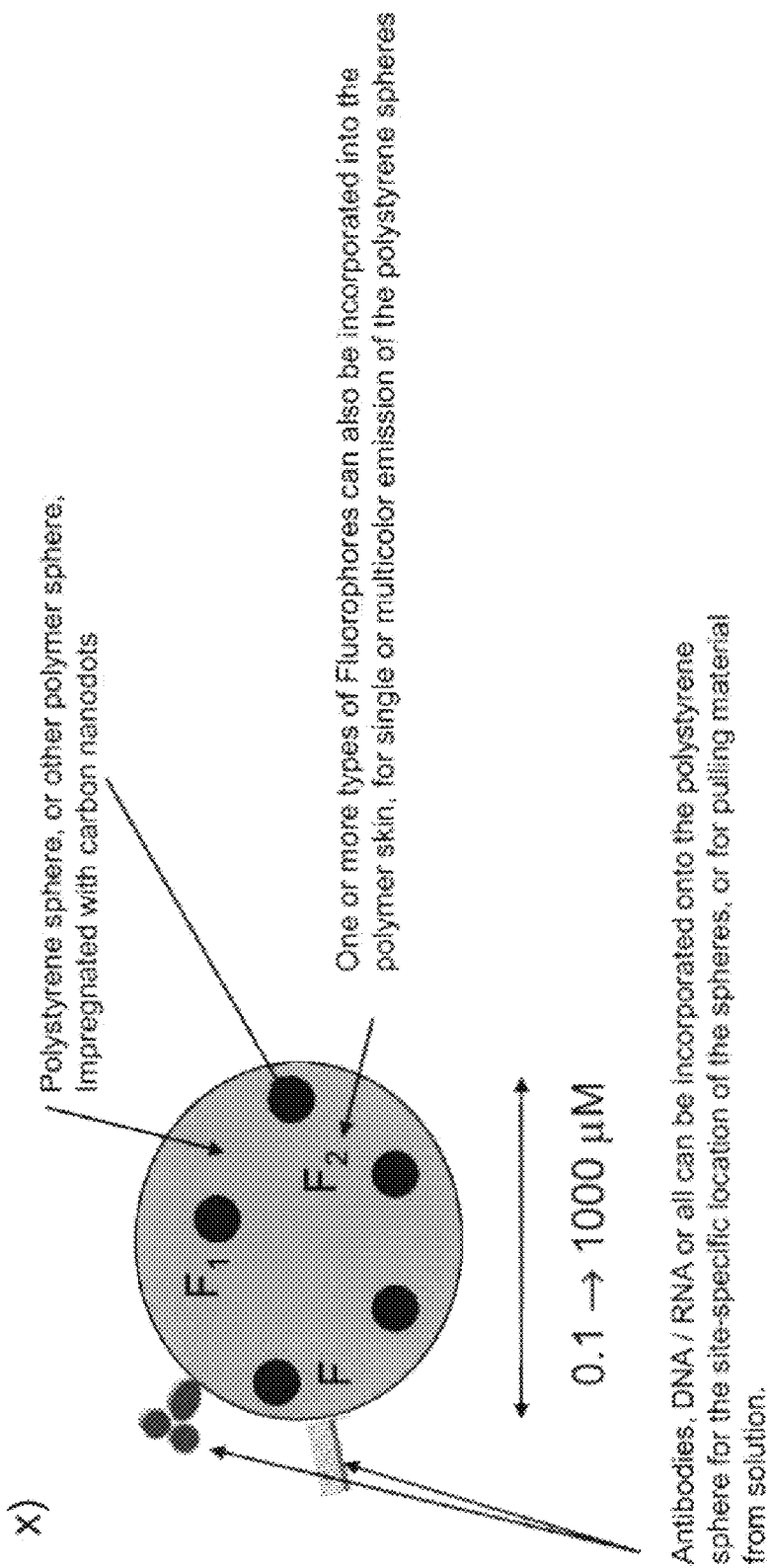
FIG. 12 shows a polymer substrate that includes carbon dots embedded into the polymeric material. Attachments on the polymeric surface may include antibodies, nucleotides sequences and/or fluorophores.

FIG. 12 shows that a polymeric substrate may include carbon nanodots either on the surface or embedded therein. Such a polymeric surface may be functionalized by adding antibodies, DNA, RNA, and even fluorophores to the polymeric material or in the alternative to the carbon dots.

TABLE 1

Fluorescence intensity decay analysis.

|  | $\tau_1$/ns | $\alpha_1$ (%) | $\tau_2$/ns | $\alpha_2$ (%) | $\tau_3$/ns | $\alpha_3$ (%) | $<\tau>$/ns | $\bar{\tau}$/ns | $\chi^2$ |
|---|---|---|---|---|---|---|---|---|---|
| CD in cuvette | 1.23 | 23.49 | 0.19 | 50.94 | 6.67 | 25.57 | .65 | 2.09 | 1.24 |
| CD glass/glass | 0.12 | 76.64 | 0.55 | 21.32 | 5.14 | 2.04 | 0.31 | 1.94 | 1.17 |
| CD glass/SIFs | 0.14 | 81.83 | 0.56 | 16.81 | 5.81 | 1.36 | 0.26 | 1.53 | 1.30 |

Figure 7:
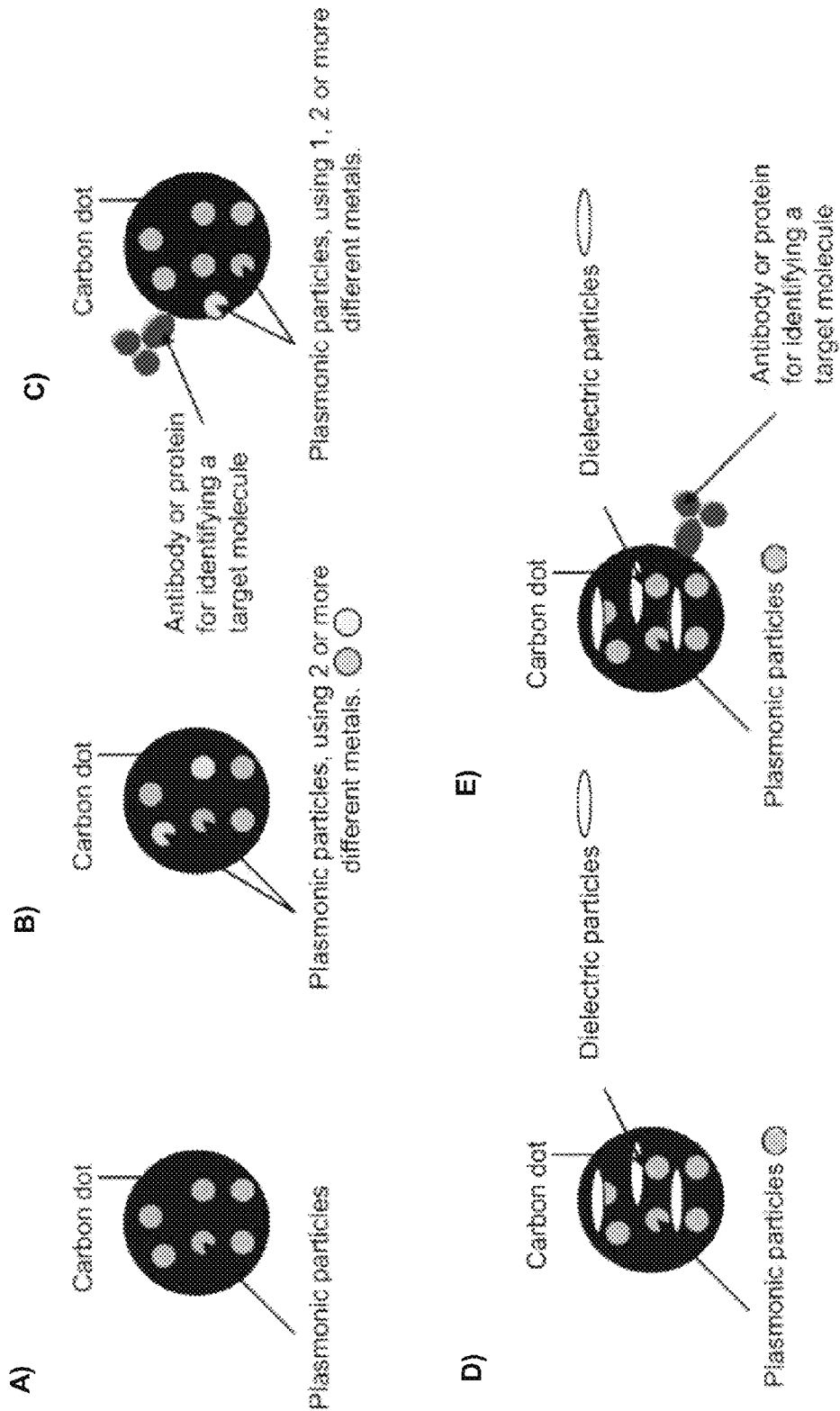
FIG. 7 shows different embodiments of carbon dots having plasmonic particle on or in the carbon dot. Dielectric materials may also be included.

$\bar{\tau}$—mean lifetime, $<\tau>$—amplitude-weighted lifetime. CD—carbon dots. Ex: 400 nm The carbon nanodots as used in the present invention can include variations in the fabrication. For example, as shown in FIG. 7, a carbon nanodot can be impregnated with metallic plasmonic particles or having such particles attached to the surface using one type of metal (A) or numerous different types (B) as described above. Further, Examples of polymeric materials include a thermoplastic, such as ethylene vinyl alcohol, a fluoroplastic such as polytetrafluoroethylene, fluoro ethylene propylene, perfluoroalkoxyalkane, chlorotrifluoroethylene, ethylene chlorotrifluoroethylene, or ethylene tetrafluoroethylene, ionomer, polyacrylate, polybutadiene, polybutylene, polyethylene, polyethylenechlorinates, polymethylpentene, polypropylene, polystyrene, polyvinylchloride, polyvinylidene chloride, polyamide, polyamide-imide, polyaryletherketone, polycarbonate, polyketone, polyester, polyetheretherketone, polyetherimide, polyethersulfone, polyimide, polyphenylene oxide, polyphenylene sulfide, polyphthalamide, polysulfone, or polyurethane.

It has been shown herein that carbon nanodots or variants thereof are similar to regular organic fluorophores and that carbon nanodots can also show enhanced emission intensities and photostabilities from plasmon supporting substrates. Given the need for highly luminescent and photostable particles, which are both non-toxic and biocompatible, numerous approaches for carbon dots and MEF can be envisioned, such as shown below:

a. as a luminescent label in assays, DNA, RNA protein;
b. as a luminescent label in flow cytometry;
c. as a luminescent label in Single molecule Fluorescence spectroscopy;
d. as a luminescent label in Fluorescence correlation spectroscopy or other fluctuation spectroscopies;
e. for use with high throughput screening assays, in 96 well or 384 well plates;
f. in cell biology, for imaging the surface of cellular features, or biologicals;
g. in cell biology, for imaging cellular interior functions, processes and trafficking;
h. in cosmetics, such as a dye/colorant for hair or skin;
i. in clothing, as a very bright luminescent dye;
j. in safety wear or gear, where brightness is important for standing out;
k. in paints or emulsions;
l. as a label in Plasmonic Electricity applications, i.e. digital fluorescence applications;
m. as labels for DNAs or proteins;
n. as a dye/colorant for paper and paper products;
o. as a potential food colorant; and
p. to generate singlet oxygen or super oxide anion radical for the disinfection of surfaces and the killing of bugs and bacteria.

REFERENCES

The contents of all references cited herein are incorporated by reference herein for all purposes.
1. Y. Sun, B. Zhou, Y. Lin and A. Xie, *J. Am. Chem. Soc.*, 2006, 128, 7756-7757.
2. X. Xu, R. Ray, Y. Gu, H. J. Ploehn, L. Gearheart, K. Raker and W. A. Scrivens, *J. Am. Chem. Soc.*, 2004, 126, 12736-12737.
3. Q. Li, T. Y. Ohulchanskyy, R. Liu, K. Koynov, D. Wu, A. Best, R. Kumar, A. Bonoiu and P. N. Prasad, *J. Phys. Chem. C*, 2010, 114, 12062-12068.
4. S. K. Nune, P. Gunda, P. K. Thallapally, Y. Y. Lin, M. L. Forrest and C. J. Berkland, *Expert Opin. Drug Delivery*, 2009, 6, 1175-1194.
5. R. Pribik, A. I. Dragan, Y. Zhang, C. Gaydos and C. D. Geddes, *Chem. Phys. Lett.*, 2009, 478, 70-74.
6. C. D. Geddes and J. R. Lakowicz, *J. Fluoresc.*, 2002, 12, 121-129.
7. K. Aslan, Z. Leonenko, J. R. Lakowicz and C. D. Geddes, *J. Fluoresc.*, 2005, 15, 643-654.
8. Y. Zhang, A. Dragan and C. D. Geddes, *J. Phys. Chem. C*, 2009, 113, 12095-12100.
9. H. Gonsalves and J. C. G. Esteves da Silva, *J. Fluoresc.*, 2010, 20, 1023-1028.
10. A. Dragon and C. D. Geddes, *Phys. Chem. Chem. Phys.*, 2010, 13, 3831-3838.

That which is claimed is:

1. A method for increasing detectable emissions from excited and variant carbon nanodots, the method comprising:
   providing metallic particles, wherein the metallic particles are immobilized on a surface substrate and the metallic particles are nanostructures, islands, or colloids;
   introducing at least one variant carbon nanodot for positioning near the metallic particles, wherein the variant carbon nanodot has a diameter of about 50 to 80 nm and consists of carbon and inclusions of metallic materials of silver, gold, copper, aluminum, iron, zinc, rhodium, indium, platinum and combination thereof and is capable of emitting a detectable signal upon excitation and positioned from about 5 nm to 200 nm from the metallic particles;
   applying electromagnetic energy in a wavelength range of from about 400 nm to 500 nm to excite the variant carbon nanodot; and
   measuring the emission from the variant carbon nanodot, wherein proximity to the metallic particles increase emission and detectable signal.

2. The method of claim 1, wherein capture receptors are attached to the metallic particles, wherein the capture receptors are specific for a target compound.

3. The method of claim 1, wherein the metallic particles have geometric shapes selected from the group consisting of spherical, triangular, elliptical, rod shape, hexagonal or multifaceted.

4. The method of claim 1, wherein the metallic particles are fabricated from silver, gold, copper, zinc, nickel, iron, rhodium, indium, palladium, aluminum, platinum or mixture thereof.

5. The method of claim 2, wherein the variant carbon nanodots are communicatively connected to the target product.

6. The method of claim 5, wherein the variant carbon nanodots are attachable to detecting probes having affinity for the target compound.

7. The method of claim 1, wherein the surface substrate is a polymeric material, glass, paper, nitrocellulose or combinations thereof.

8. The method of claim 2, further comprising applying ultrasound or microwave energy in an amount sufficient to increase movement of the target compound to the capture receptors thereby increasing reactions within the system.

9. The method of claim 2, wherein the target compound is a nucleotide sequence and the capture receptors are nucleotide probes having affinity for a first sequence of the target compound.

10. The method of claim 9, wherein detector probes comprising the variant carbon nanodot are nucleotide sequences having affinity for a second sequence of the target compound.

11. A method of detection of a target molecule, the method comprising:
   applying a multiplicity of metallic particles to a substrate surface used in the assay system;
   connecting capture molecules to the metallic particles, wherein the capture molecules have binding affinity for the target molecules;
   introducing a solution suspected of including the target molecules;
   introducing detector molecules having affinity for the target molecules, wherein the detector molecules comprises at least one variant carbon nanodot and upon binding of detector molecule the variant carbon nanodot is positioned a distance from about 5 nm to about 50 nm from the metallic particles, wherein the variant carbon nanodot has a diameter of about 50 to 80 nm and consists of carbon and inclusions of metallic materials of silver, gold, copper, aluminum, iron, zinc, rhodium, indium, platinum and combination thereof; and applying electromagnetic energy in a wavelength range of from about 400 nm to 500 nm to excite the variant carbon nanodot; and measuring any emission signal from the excited variant carbon nanodot, wherein proximity of the at least one variant carbon nanodot to the metallic particles increases emission and detectable signal.

12. The method of claim 11, wherein the metallic particles have geometric shapes selected from the group consisting of spherical, triangular, elliptical, rod shape, hexagonal or multifaceted.

13. The method of claim 11, wherein the metallic particles are fabricated from silver, gold, copper, zinc, nickel, iron, rhodium, indium, palladium, aluminum, platinum or mixture thereof.

14. The method of claim 11, wherein the surface substrate is a polymeric material, glass, paper, nitrocellulose or combinations thereof.

* * * * *